(12) United States Patent
Freiin Von Kapri et al.

(10) Patent No.: US 12,290,327 B2
(45) Date of Patent: May 6, 2025

(54) ADJUSTABLE USER CONSOLE FOR A SURGICAL ROBOTIC SYSTEM

(71) Applicant: Verb Surgical Inc., Santa Clara, CA (US)

(72) Inventors: Anette Lia Freiin Von Kapri, Mountain View, CA (US); Joan Savall, Palo Alto, CA (US); Denise Ann Miller, Scotts Valley, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/487,392

(22) Filed: Oct. 16, 2023

(65) Prior Publication Data

US 2024/0033023 A1 Feb. 1, 2024

Related U.S. Application Data

(63) Continuation of application No. 17/020,722, filed on Sep. 14, 2020, now Pat. No. 11,826,115.

(51) Int. Cl.
*A61B 17/00* (2006.01)
*A61B 34/00* (2016.01)
*A61B 34/35* (2016.01)
*A61B 90/60* (2016.01)
*B25J 13/06* (2006.01)

(52) U.S. Cl.
CPC .............. *A61B 34/35* (2016.02); *A61B 34/25* (2016.02); *A61B 90/60* (2016.02); *B25J 13/06* (2013.01); *A61B 2017/00216* (2013.01); *A61B 2017/00973* (2013.01)

(58) Field of Classification Search
CPC ......... A61B 34/35; A61B 34/25; A61B 90/60; A61B 2017/00216; A61B 2017/00973; A61B 34/37; A61B 34/74; A61B 2034/2048; A61B 2034/2051; A61B 2090/372; A61B 90/361; A61B 34/20; A61B 2034/252; B25J 13/06; B25J 13/00; B25J 13/02; B25J 13/04
See application file for complete search history.

(56) References Cited

U.S. PATENT DOCUMENTS

| 9,794,516 | B1 | 10/2017 | Tuli |
|---|---|---|---|
| 2008/0158096 | A1 | 7/2008 | Breed |
| 2012/0085267 | A1 | 4/2012 | Kenny |
| 2017/0059872 | A1 | 3/2017 | Banyay |
| 2017/0165014 | A1 | 6/2017 | Nakanishi |
| 2018/0078034 | A1 | 3/2018 | Savall |
| 2019/0220091 | A1* | 7/2019 | Yu ........................ G06F 1/1601 |
| 2020/0012116 | A1* | 1/2020 | Fuerst .................... G02B 30/26 |

(Continued)

*Primary Examiner* — Harry Y Oh
(74) *Attorney, Agent, or Firm* — Aikin & Gallant, LLP

(57) ABSTRACT

A method performed by a surgical robotic system that includes a seat that is arranged for a user to sit and a display column that includes at least one display for displaying a three-dimensional (3D) surgical presentation. The method includes receiving an indication that the user has manually adjusted the seat and in response, determining, while the user is sitting on the seat, a position of the user's eyes, determining a configuration for the display column based on the determined position of the user's eyes, and adjusting the display column by actuating one or more actuators of the display column according to the determined configuration.

21 Claims, 7 Drawing Sheets

(56) References Cited

U.S. PATENT DOCUMENTS

| | | |
|---|---|---|
| 2020/0138534 A1* | 5/2020 | Garcia Kilroy ........ A61B 34/20 |
| 2020/0260878 A1 | 8/2020 | Kuo |
| 2020/0304753 A1* | 9/2020 | Venkataraman ... A61B 1/00045 |
| 2022/0075191 A1 | 3/2022 | Rittger |

* cited by examiner

ADJUSTABLE USER CONSOLE FOR A SURGICAL ROBOTIC SYSTEM

CROSS-REFERENCE TO RELATED APPLICATION

This application is a continuation application of co-pending U.S. patent application Ser. No. 17/020,722, filed on Sep. 14, 2020, which is incorporated by reference herein.

FIELD

Various aspects of the disclosure relate generally to surgical robotic systems, and more specifically to a surgical robotic system that includes an adjustable user console. Other aspects are also described.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Control inputs from a user (e.g., surgeon or other operator) are captured via one or more user input devices and then translated into control of the robotic system. For example, in response to user commands, a tool driver having one or more motors may actuate one or more degrees of freedom of a surgical tool when the surgical tool is positioned at the surgical site in the patient.

SUMMARY

A surgical robotic system may include a user console at which a user (e.g., surgeon) may perform a remote surgical procedure, e.g., teleoperation. The console may include a chair (or a seat) at which the user sits and one or more user-input devices (UIDs), such as a handheld UID and a foot-operated control (e.g., foot pedal). To perform the remote surgical procedure, the user manipulates the UIDs (e.g., pressing down on the foot-operated control, pressing a button on the handheld UID, moving the handheld UID, etc.) in response to which the system controls one or more components of the surgical robotic system, such as a surgical tool coupled to a robotic arm. The console may also include a display that presents (or displays) a view of a surgical site (which may be inside the patient during a laparoscopic surgery). The display may also show the surgical tool with which the user is performing the surgery.

During setup of the system, the user may first configure the user console. For instance, the user may adjust (or adapt) the seat for comfort (e.g., adjusting a height of the seat, armrest position, etc.). These ergonomic adjustments are one of the most important setup tasks because the user may be sitting in the seat for extended periods of time during a surgical procedure. Once the seat is in a user-preferred position, the user may configure other components at the user console, such as the position of the UIDs for a comfortable reach, and the position of the display (e.g., adjusting a height of the display, etc.).

The initial setup tasks for configuring the user console may be prone to human error. For example, the user may accidently omit a part of the user console configuration (e.g., forgetting to adjust the foot pedal), which may cause the user discomfort while using the user console. In addition, some ergonomic adjustments may inadvertently create a less optimal operating configuration of the system by adversely affecting the operating efficiency of some components within the system. This may be due to the lack of physical feedback. For example, when adjusting the seat, the user will be able to configure the seat to a user-preferred position based on a level of comfort. In contrast, when configuring a display screen (e.g., the position of the display screen with respect to the seat), the user will not inherently know the best or most optimal viewing position at which to view the screen, which may be defined by the manufacturer or by the content that is to be displayed on the screen. As a result, although the user's seat may be set at a desired comfort level, when seated the user may be at a less optimal viewing position (e.g., too far away from the display screen, looking at the screen from an angle, etc.) Therefore, there is a need for an adjustable user console that may be automatically (e.g., without user intervention) configured such that the user console satisfies the user's ergonomic adjustments as well as having the most optimal operating configuration.

The present disclosure provides an adjustable user console of a surgical robotic system that includes a seat that is arranged for the user to sit and a display column that includes at least one display for displaying a 3D surgical presentation. The system may receive an indication that the user has manually adjusted the seat. For instance, the user may operate a control panel of the seat to adjust one or more degrees of freedom associated with the seat (e.g., seat height, seat base tilt, etc.). The system may determine, using an eye tracking system and while the user is sitting on the seat, a position of the user's eyes. Such a system may include a camera that is arranged to capture image data with which the system uses to perform object recognition to identify the user's eyes. The system determines a configuration of the display column (e.g., a height at which the display column is to be positioned and a location at which the display column is to be positioned with respect to the seat, etc.) based on the position of the user's eyes. Specifically, the system determines how high the display is to be positioned (e.g., a vertical adjustment of the display) and a displacement of the display column. The system adjusts the display column by actuating one or more actuators of the display column according to the determined configuration. Thus, the adjustment of the display column may provide the user with the most optimal viewing experience, while the seat is at a user-preferred position. In addition, the performed adjustments may reduce the complexity of the initial user setup, since the display column is automatically adjusted by the system, rather than having to be manually adjusted by the user.

In one aspect, the surgical robotic system may include a robotic arm and a UID that is arranged to control the robotic arm when being held and manipulated by the user. The system may determine a user-desired position at which the user is to manipulate the UID while the user sits on the seat. For instance, this position may be a comfortable position (e.g., where the user's arms are resting on the seats armrests) and/or may be a position in which the user has a maximum range of motion. In this case, the system may further determine the configuration based on the user-desired position.

In another aspect, the system may determine the user-desired position according to the adjusted configuration of the seat. For example, the system may determine a base height of a base of the seat and an armrest height that represents a distance between the base of the seat and an armrest. From the base height and the armrest height, the system may determine (or estimate) the user-desired position. In another aspect, the user-desired position may be explicitly defined by the user. For instance, the system may determine, using a UID tracking system, a position of the UID. The system may receive a user-selection (e.g., via a user interface (UI) item presented in a graphical user interface (GUI) presented on the display) defining the position of the UID as the user-desired position.

In one aspect, the surgical robotic system may include one or more "workspaces" that are areas (or volumes) of space positioned about the adjustable user console that are each associated with an operation of a particular component of the system. For example, when the display is a 3D immersive display, the system may include a 3D perception workspace that is a volume in front of the display. While inside the workspace (e.g., while the user's eyes are inside the workspace), the user may perceive an optimal 3D immersive presentation (e.g., the best stereoscopic presentation). But while outside the workspace, the user may not perceive such an optimal presentation (e.g., objects may lose depth). As another example, the system may include an eye tracking workspace that is an area at which both (or at least one) of the user's eyes may be tracked by the eye tracking system. In one aspect, the eye tracking workspace may be an area that is within the field of view of the eye tracking system's camera, which may be coupled to the display column. As another example, the system may include a UID tracking workspace that is an area in which the UID may be held and manipulated by the user in order to control a robotic arm. In particular, the UID workspace may represent an area in which a sensor may (e.g., efficiently) track movements and/or manipulations of a user-held UID, which may be used by the system to control a movement of a robotic arm. When the UID is outside this workspace, however, the system may not be able to efficiently track the UID. As a result, when the UID is outside the workspace, the system may hold (or pause) control of the robotic arm.

In one aspect, the configuration of the display column may be determined such that requirements of all (or at least some of the) workspaces are satisfied (e.g., both of the user's eyes are inside the 3D perception workspace and the eye tracking workspace.) For example, the system may determine, with respect to the position of the user's eyes, a position of the 3D perception workspace, a position of the eye tracking workspace, and a position of the UID tracking workspace. The system may determine, using the eye tracking system, whether the eyes of the user are outside of either the 3D perception workspace or the eye tracking workspace; and may determine, using the UID tracking system, whether the UID is outside the UID tracking workspace. In response to determining that the position of the user's eyes is outside the 3D perception workspace or the eye tracking workspace, or the UID is outside the UID tracking workspace, the system determines an adjustment to the configuration of the display column such that 1) the position of the user's eyes is inside the 3D perception workspace and the eye tracking workspace and 2) the UID is inside the UID tracking workspace.

The above summary does not include an exhaustive list of all aspects of the disclosure. It is contemplated that the disclosure includes all systems and methods that can be practiced from all suitable combinations of the various aspects summarized above, as well as those disclosed in the Detailed Description below and particularly pointed out in the claims. Such combinations may have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect of this disclosure are not necessarily to the same aspect, and they mean at least one. Also, in the interest of conciseness and reducing the total number of figures, a given figure may be used to illustrate the features of more than one aspect, and not all elements in the figure may be required for a given aspect.

DETAILED DESCRIPTION

Several aspects of the disclosure with reference to the appended drawings are now explained. Whenever the shapes, relative positions and other aspects of the parts described in a given aspect are not explicitly defined, the scope of the disclosure here is not limited only to the parts shown, which are meant merely for the purpose of illustration. Also, while numerous details are set forth, it is understood that some aspects may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
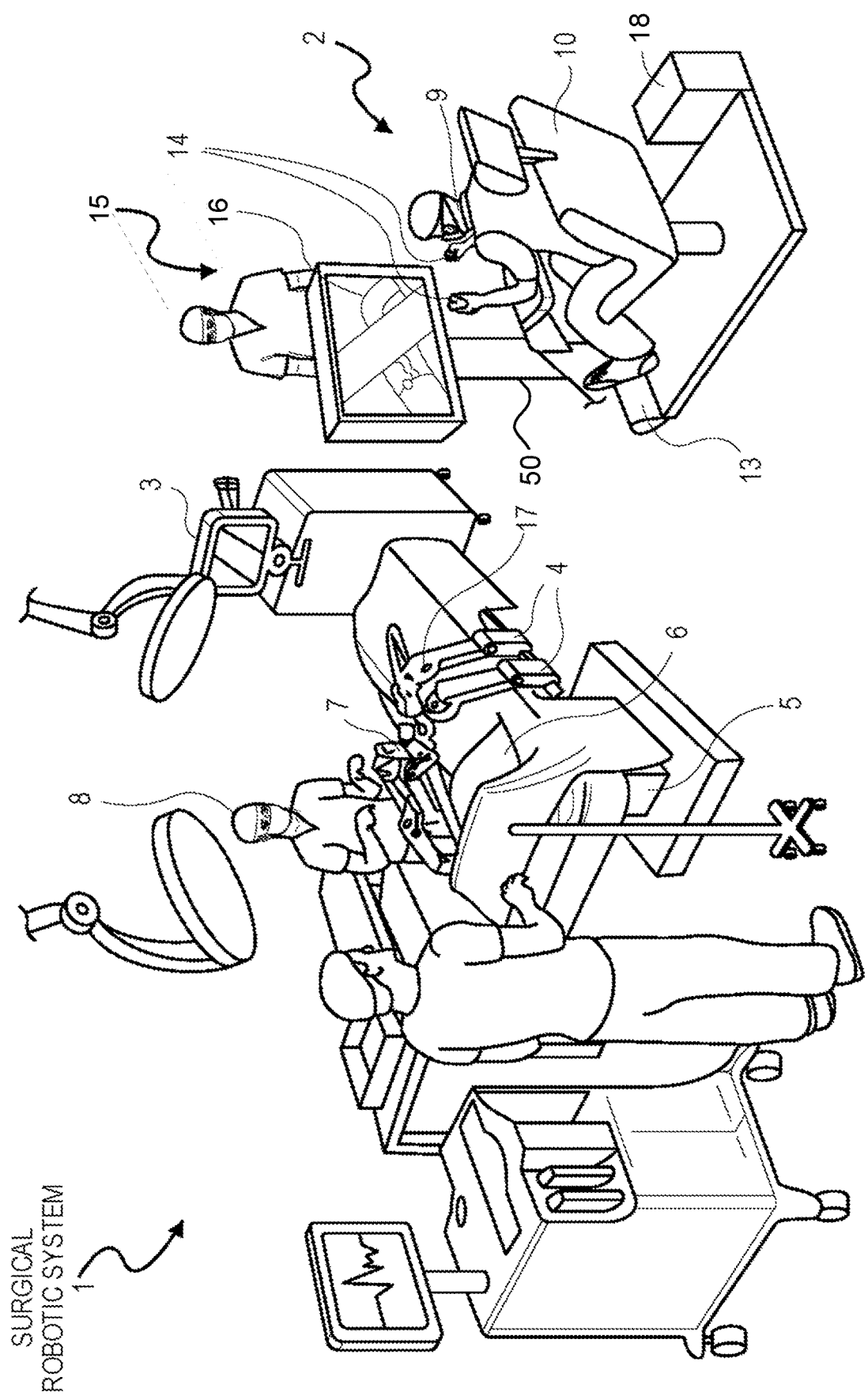
FIG. 1 shows a pictorial view of an example surgical robotic system in an operating arena.

FIG. 1 shows a pictorial view of an example surgical robotic system 1 in an operating arena. The robotic system 1 includes a user console 2, a control tower 3, and one or more surgical robotic arms 4 at a surgical robotic table (surgical table or surgical platform) 5. In one aspect, the arms 4 may be mounted to a table or bed on which the patient rests as shown in the example of FIG. 1. In one aspect, at least some of the arms 4 may be configured differently. For example, at least some of the arms may be mounted on a ceiling, sidewall, or in another suitable structural support, such as a cart separate from the table. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an aspect, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may include one or more components, such as a seat 10, one or more foot-operated controls (or foot pedals) 13, one or more (handheld) user-input devices (UIDs) 14, and a display column 15. The display column 15 includes at least one (user) display 16 that is configured to display, for example, a view of the surgical site inside the patient 6. As shown, the display is coupled to (or disposed on) top (or at a top end) of a vertical support 50 that is extending upward from the ground (or floor). In some aspects, the vertical support may be arranged to support (or hold) two or more displays. The display may be configured to display image data (e.g., still images and/or video). In one aspect, the display may be any type of display, such as a liquid crystal display (LCD), a light-emitting diode (LED) display, an organic LED (OLED) display, etc. In some aspects, the display may be a 3D immersive display that is for displaying 3D (surgical) presentations. For instance, during a surgical procedure one or more endoscopic cameras may be capturing image data of a surgical site, which the display presents to the user in 3D. In one aspect, the 3D display may be an autostereoscopic display that provides 3D perception to the user without the need for special glasses. As another example, the 3D display may be a stereoscopic display that provides 3D perception with the use of glasses (e.g., via active shutter or polarized).

In another aspect, the display 16 may be configured to display at last one graphical user interface (GUI) that may provide informative and/or interactive content, to thereby assist a user in performing a surgical procedure with one or more robotic instruments in the surgical robotic system 1. For example, some of the content displayed may include image data captured by one or more endoscopic cameras, as described herein. In another aspect, the GUI may include selectable UI items, which when manipulated by the user may cause the system to perform one or more operations. For instance, the GUI may include a UI item as interactive content to switch control between robotic arms. In one aspect, to interact with the GUI, the system may include input devices, such as a keyboard, a mouse, etc. In another aspect, the user may interact with the GUI using the UID 14. For instance, the user may manipulate the UID to navigate through the GUI, (e.g., with a cursor), and to make a selection may hover the cursor over a UI item and manipulate the UID (e.g., selecting a control or button). In some aspects, the display may be a touch-sensitive display screen. In this case, the user may perform a selection by navigating and selecting through touching the display. In some aspects, any method may be used to navigate and/or select a UI item.

As shown, the remote operator 9 is sitting in the seat 10 and viewing the user display 16 while manipulating a foot-operated control 13 and a handheld UID 14 in order to remotely control the arms 4 and the surgical tools 7 (that are mounted on the distal ends of the arms 4.) In one aspect, the user console may be an adjustable user console that is configured to adjust one or more components (e.g., the display column 15) according to a user's preferred console position. More about the adjustable user console is described herein.

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one aspect, the remote operator 9 holds and moves the UID 14 to provide an input command to drive (move) one or more robotic arm actuators 17 (or driving mechanism) in the robotic system 1 for teleoperation. The UID 14 may be communicatively coupled to the rest of the robotic system 1, e.g., via a console computer system 18 (or host). The UID 14 can generate spatial state signals corresponding to movement of the UID 14, e.g. position and orientation of the handheld housing of the UID, and the spatial state signals may be input signals to control motions of the robotic arm actuators 17. The robotic system 1 may use control signals derived from the spatial state signals, to control proportional motion of the actuators 17. In one aspect, a console processor of the console computer system 18 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some aspects, the communication between the surgical robotic table 5 and the user console 2 may be through a control tower 3, which may translate user commands that are received from the user console 2 (and more particularly from the console computer system 18) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable ones of a variety of data communication protocols, such as BLUETOOTH protocol. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
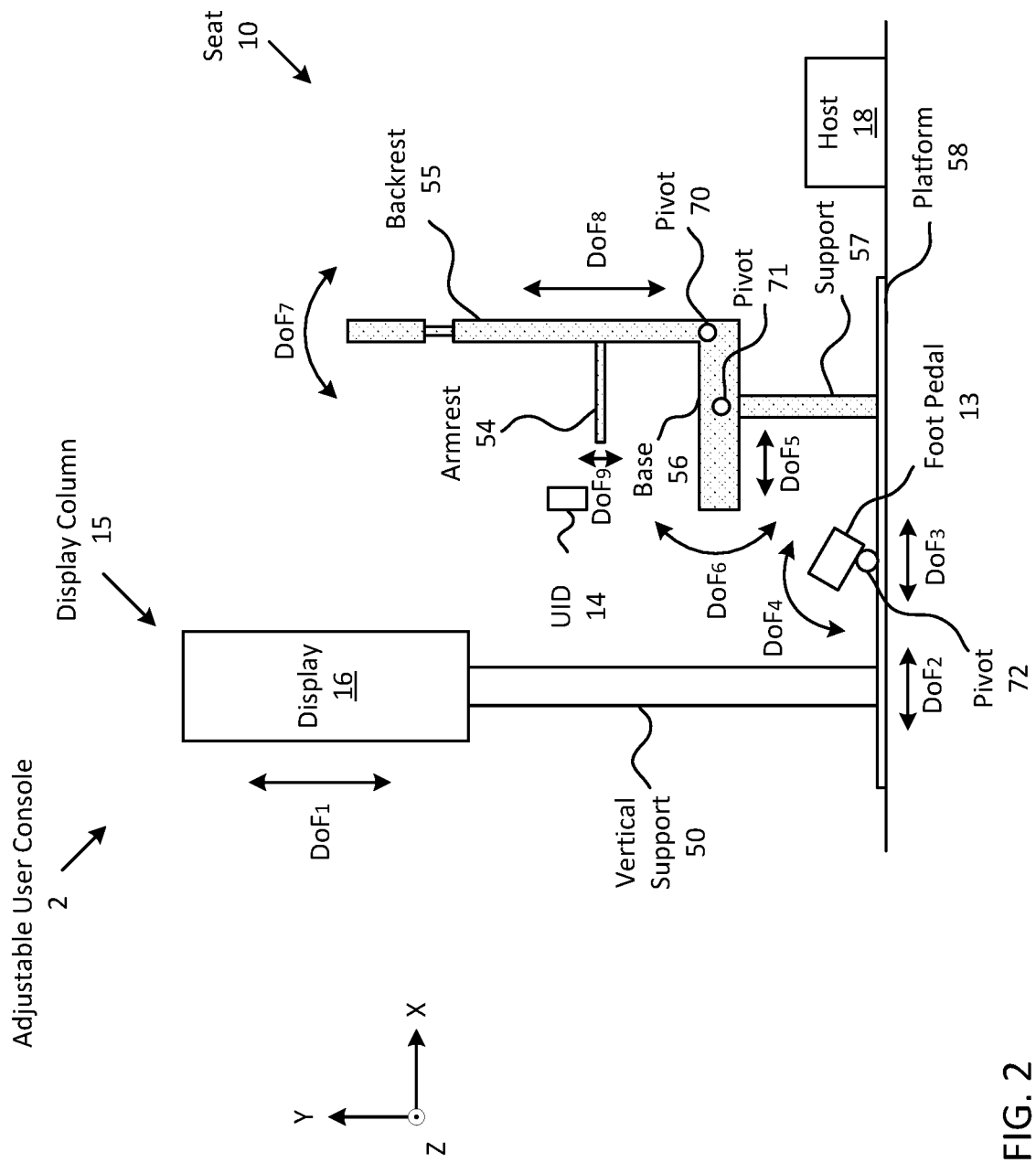
FIG. 2 shows an adjustable user console of the surgical robotic system according to one aspect.

FIG. 2 shows an adjustable user console (or user console) 2 of the surgical robotic system 1 according to one aspect. Specifically, this figure shows nine degrees of freedom (DoF) along which at least some of the components of the adjustable user console may independently move with respect to the user console (and/or one another). As shown, the display column 15 includes two degrees of freedom, the foot pedal 13 includes two degrees of freedom, and the seat 10 includes five degrees of freedom. In one aspect, the adjustable user console may include more or less degrees of freedom. For instance, as shown, the display column includes two degrees of freedom, one in a vertical (or Y-axis) and one in a horizontal (or X-axis). In some aspects, the display column may have at least one additional degree of freedom along the Z-axis, such that the display column may be arranged to move along either axis. As another example, the seat 10 may include at least one additional degree of freedom, such as a rotational degree of freedom in which the seat may rotate about a vertical (Y-axis) that runs through (e.g., the support 57 of) the seat 10.

As described herein, the display column includes two degrees of freedom, $DoF_1$ and $DoF_2$. $DoF_1$ represents vertical movement (or translation) of the display 16 along the Y-axis. For instance, the display may be arranged to move vertically such that the height of the display that is mounted to the vertical support 50 is adjustable. In one aspect, the display column may include a telescoping mechanism that includes one or more actuators (e.g., actuators 25 shown in FIG. 3) that are arranged to move the display along the Y-axis. For instance, a bottom of the telescoping mechanism may be coupled to the top of the vertical support, and a top of the mechanism may be coupled to the (e.g., bottom of the) display. As the mechanism moves vertically, the height of the display may change. In another aspect, the vertical support may include the telescoping mechanism (as part of or coupled to the vertical support) that is arranged to expand in the vertical direction in order to increase the height of the display, and is arranged to retract in order to decrease the height. In some aspects, the display may be attached (or mounted) to the vertical support 50 via a rail (not shown), which is arranged to allow the display to slide up and down the vertical support.

The second degree of freedom, $DoF_2$, represents horizontal movement (or displacement) of the display column 15 along the X-axis. The display column may be arranged to move along this axis in order to adjust the distance between the display column and the seat 10. Specifically, the display column may include one or more (additional) actuators 25 that are arranged to drive the display column toward or away from the seat 10. In one aspect, the display column may include one or more casters (not shown) that are disposed at a bottom of the vertical support 50 and are arranged to wheel the display column towards or away from the seat. In this case, the actuators may drive the casters to propel the display column. In one aspect, the casters may be rotatable casters (e.g., swivel casters), which are arranged to move in any direction (along the ZX-plane). Thus, the display column may be displaced along the ZX-plane with respect to the seat 10. As shown, the display column may be positioned on top of a platform 58. In some aspects, the display column may be coupled to the platform via one or more rails (not shown), which may run in the X-direction. In this case, the vertical support may include a rotating mechanism that is rotatably coupled to the rails, and is driven by the actuators to slide along the rails. Thus, in this example, the display column may move in $DoF_2$ by sliding along the rails.

The foot pedal 13 includes two degrees of freedom, $DoF_3$ and $DoF_4$. $DoF_3$ represents movement of the foot pedal along the X-axis. The foot pedal may be arranged to move along this axis in order to adjust the distance between the foot pedal and the seat 10. In one aspect, any method (or mechanism) may be used to move the foot pedal, such as casters and/or a rail, as described with respect to $DoF_2$ of the display column 15. $DoF_4$ represents rotational movement (or tilting) of the foot pedal around pivot 72, about the Z-axis. For example, the foot pedal may include a tilting mechanism that has one or more actuators (e.g., actuators 27 of FIG. 3) that are arranged to pivot (or rotate) the food pedal around pivot 72.

The seat includes several elements, such as at least one support (or leg) 57, a base (or seat) 56, a backrest 55 (which includes a headrest), and at least one armrest 54. In one aspect, the seat may include several legs, each of which supporting the base. As described herein, the seat includes five degrees of freedom, $DoF_5$-$DoF_9$. $DoF_5$ represents movement of the seat base along the X-axis. Specifically, the base (including the backrest and armrest) is arranged to move forward and backward with respect to the support 57 (which may remain stationary). For example, the base may include a rail (not shown) that is mounted to (a top end of) the support 57. The base may also include one or more actuators (e.g., actuators 26 of FIG. 3) that are arranged to drive the base back and forth about the top end of the support. In some aspects, the entire seat (including the support 57) may be arranged to move in $DoF_5$. For instance, the support 57 may be movably coupled to rails of the platform 58 or may have casters, as described herein with respect to the display column 15 and the foot pedal 13. In another aspect, the seat may include another degree of freedom in which the base 56 may move along the Z-axis with respect to the support 57, thereby allowing the seat 10 to move side-to-side and back and forth.

$DoF_6$ represents rotational movement (or tilting) of the base 56 of the seat around pivot 71, about the Z-axis. Thus, this degree of freedom allows the (base of the) seat to tilt forwards or backwards, thereby shifting the weight of the user based on the direction of tilt. $DoF_7$ represents rotational movement of the backrest 55 around pivot 70, about the Z-axis. This degree of freedom allows the user to recline the backrest. In one aspect, the seat may be arranged to perform such rotational movements, using separate tilting mechanisms, as described herein.

$DoF_8$ represents movement of the seat in the Y-axis. For instance, the seat may be arranged to move vertically such that the height of the (base 56 of the) seat 10 is adjustable. In one aspect, any method (or mechanism) may be used to adjust the height of the seat, such as a telescoping mechanism, as described with respect to $DoF_1$ of the display column 15. $DoF_9$ represents movement of the armrest 64 in the Y-axis. For instance, the armrest may be arranged to move vertically such that the height (distance) between the base 56 and the armrest changes. In one aspect, any method (or mechanism) may be used to adjust the height of the seat and armrest, as described herein. For instance, the support 57 may include a telescoping portion, while the backrest 55 may include at least one rail to which the armrest is slidably attached in order to allow the armrest to slide up and down.

As shown, the display column 15, the foot pedal 13, and the seat 10 are each attached (or mounted) to the platform 58. In one aspect, however, at least some of the components may be mounted to a floor. For instance, the foot pedal and the display column may be separate from the platform 58, while the seat remains mounted to the platform, as illustrated in FIG. 1.

Figure 3:
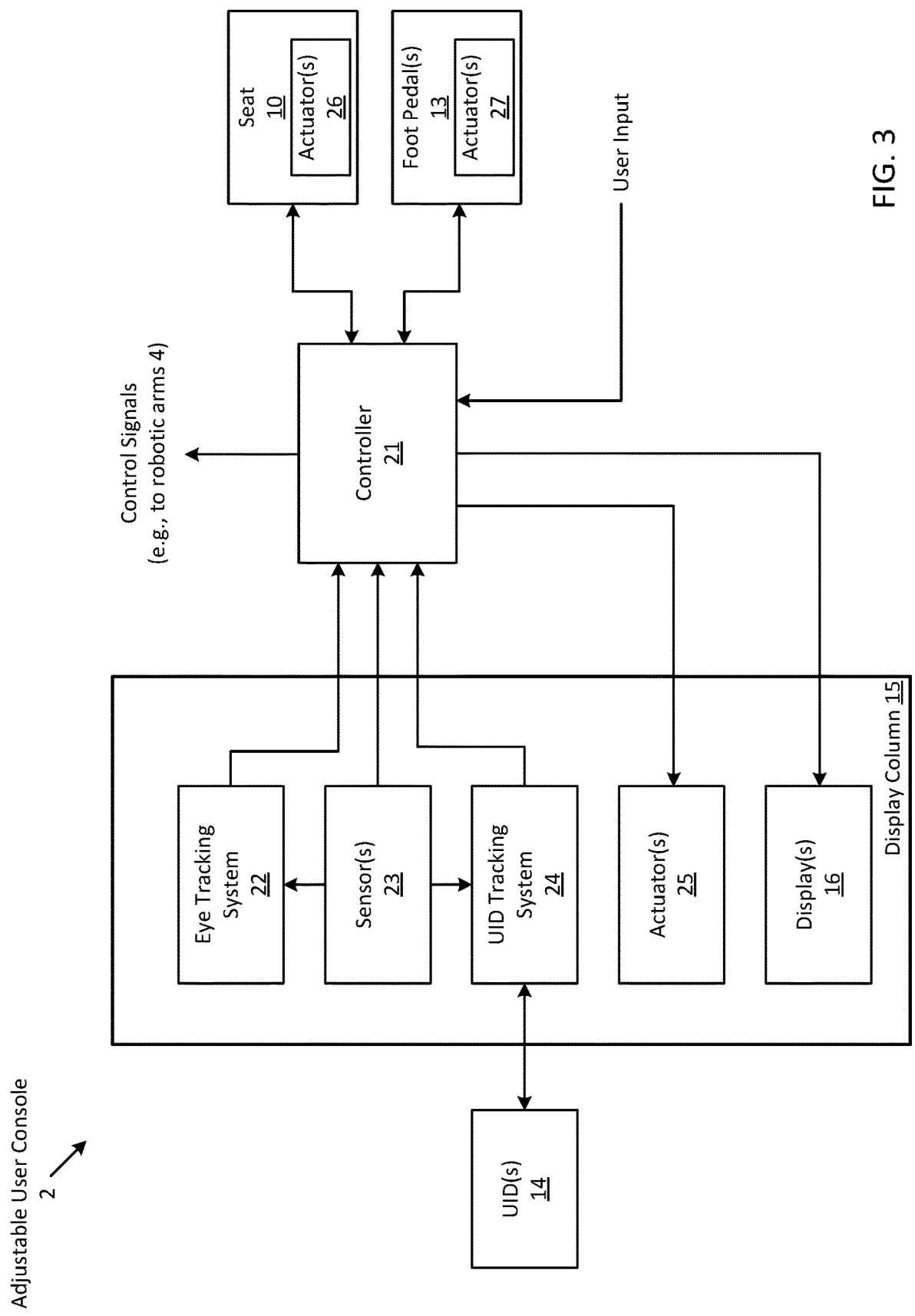
FIG. 3 is a block diagram of the adjustable user console of the surgical robotic system according to one aspect.

FIG. 3 is a block diagram of the adjustable user console 2 of the surgical robotic system 1 according to one aspect. The block diagram includes one or more UIDs 14, the display column 15, a controller 21, the seat 10, and one or more foot pedals 13. As described herein, the (controller 21 of the) adjustable user console 2 (or more generally the surgical robotic system 1) is configured to control one or more components (e.g., the arms 4) of the system according to how one or more UIDs and/or one or more foot pedals are manipulated by the user (e.g., moving the UID, a user-selection of an input on the UID, pressing down on the foot pedal, etc.). In one aspect, the controller may be configured to control a robotic arm according to how the UID is held and manipulated by the user. For example, a robotic arm may mirror similar movements of a UID (e.g., panning a UID from left to right may pan the arm from left to right).

In one aspect, the UID may be a "grounded" UID, which is an input device that is mechanically tied or tethered (e.g., that is wired or coupled) to the adjustable user console 2. For example, the UID 14 may be wired such that when (held and) manipulated by the user, the UID has a limited range of motion. As another example, the UID may be (e.g., fixedly) coupled to the armrest 54 of seat 10, as shown in FIG. 2, such that when the user releases the UID it stays in a relatively same position. In another aspect, the UID may be a "floating" or "ungrounded" UID, which is an input device that is not mechanically tied or tethered to the user console. Such a UID may be a wireless input device that communicates with the (e.g., host 18) via any wireless communication protocol (e.g., BLUETOOTH protocol). In which case, the user may manipulate the UID by moving the UID within a general vicinity of the user console. As described herein, the UID 14 may communicate with the user console via the UID tracking system 24. In another aspect, the UID may be a handheld UID.

As described herein, the display column 15, the seat 10, and foot pedal 13, each include one or more actuators 25, 26, and 27, respectively. Specifically, they may each include one or more actuators (or motors), which when actuated adjusts one or more components along at least one degree of freedom, as described herein. In one aspect, the actuators may actuate in response to receiving one or more control signals (from the controller 21). The display column 15 may include at least two actuators 25, a first actuator (e.g., that may be a part of a telescoping mechanism, as described herein) that is arranged to move the display 16 in $DoF_1$ (e.g., along a vertical axis to adjust the height of the display), and a second actuator that is arranged to move the display column in $DoF_2$ (e.g., along a horizontal axis to adjust the distance between the display column and the seat 10). As another example, the foot pedal 15 may include at least two actuators 27, one actuator that is arranged to move the foot pedal in $DoF_3$, and another actuator (e.g., that may be a part of a tilting mechanism, as described herein) that is arranged to rotate (or tilt) the foot pedal around the pivot 72 in $DoF_4$. In addition, the seat 10 may include at last five actuators, each actuator arranged to move and/or tilt the components of the seat in a respective degree of freedom (e.g., $DoF_5$-$DoF_9$).

In one aspect, the adjustable user console 2 may be arranged such that a user may manually adjust a configuration of the console. Specifically, the user may adjust the configuration by adjusting the display column 15, the seat 10, and/or the foot pedal 13. In one aspect, the console may be adjusted in response to receiving user input. In particular, the controller 21 may be configured to receive user input that represents user commands for adjusting the console. For example, the console may include a control panel (not shown) or a control interface that the user may operate in order to adjust the configuration. The control panel may include one or more controls, each associated with a particular degree of freedom. As an example, one control may set (or adjust) the height of the seat ($DoF_8$). When selected (e.g., to increase the height), the control panel may transmit the user input (as a control signal) to the controller 21, which then may transmit the control signal to one or more actuators of the seat. In response, the base 56 of the seat 10 may move upward. In one aspect, the user input may be received via user-interaction with a GUI displayed on the display 16, as described herein. In one aspect, the amount at which the seat moves may be based on the duration in which the user selects and holds the control. In another aspect, the seat may move a predetermined distance each time the control is selected. User inputs may be received via other methods, such as voice commands that are captured by one or more microphones, which is then transmitted to the controller. In another aspect, at least some of the components of the console may include a control panel, such as the seat. In this case, when the seat's control panel is manipulated, control signals may be sent directly to the seat's actuators. In one aspect, the seat may transmit signals to the controller 21 indicating that the movement has occurred. In another aspect, the user may manually adjust the configuration by physically moving (or tilting) a component of the user console. In another aspect, the user console 2 may be automatically adjusted by the controller 21. More about the controller adjusting the user console is described herein.

Figure 6A:
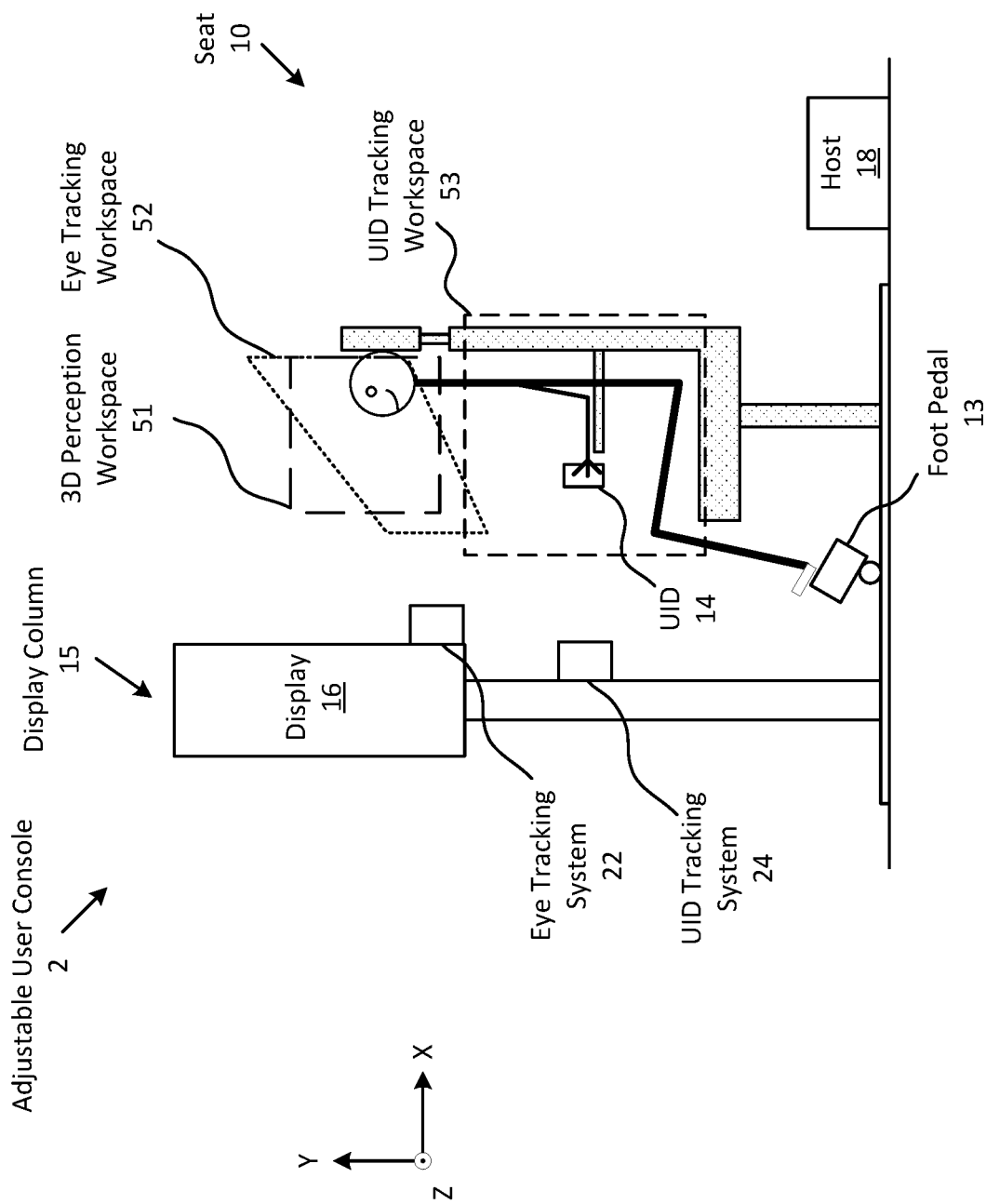
FIGS. 6A-6C show several stages in which the adjustable user console is automatically configured according to one aspect.

The display column 15 includes several components (or elements), such as one or more sensors 23, an eye tracking system 22, a UID tracking system 24, the one or more actuators 25, and one or more displays 16. In one aspect, at least some of the components may be integrated (or a part of) the display column, such that they are fixedly coupled to the column. In another aspect, at least some of the components may be movably (or removeably) coupled to the column. For instance, as illustrated in FIG. 6A, the eye tracking system 22 may be coupled to (or mounted on) the display 16, while the UID tracking system may be coupled to the vertical support 50. In some aspects, these components may be positioned differently (e.g., both systems may be coupled to the support 50). As another example, one or more of the sensors 23 may be positioned within the operating arena, as illustrated in FIG. 1.

In one aspect, at least some of the components of the display column 15 may be separate from the display column, such as being separate electronic devices. For example, the UID tracking system 24 and/or the eye tracking system 22 may each be integrated within separate electronic devices (or a same electronic device) from the display column 15. As a result, the adjustable user console 2 illustrated in FIG. 1 may include an electronic device positioned about the seat 10. When adjustments are to be made to the user adjustable console, each (or at least one) of these separate devices may be moved in a similar fashion as described with respect to the display column. More about adjusting separate devices is described herein.

The sensor 23 may be any type of sensor that is arranged to sense (or detect) environmental characteristics on or around the adjustable user console 2, and is arranged to generate sensor data (e.g., electrical signals) that indicates such characteristics. For example, the sensor may be an optical sensor, such as a camera that is arranged to capture image data of a scene within a field of view of the camera as one or more images. As another example, the sensor may include a motion sensor that is arranged to sense motion (e.g., of the user), and is arranged to produce motion data that represents such motion. In another aspect, the sensor may be a proximity sensor (e.g., an inductive sensor, a capacitive sensor, etc.), that is arranged to detect the presence or absence of objects. In one aspect, the sensor may be a microphone that is arranged to capture sound as a microphone signal. In another aspect, the sensor 23 may include an electromagnetic transmitter that includes a radio frequency (RF) transmitter (and receiver) that is configured to establish a wireless connection with a wireless device (e.g., a wireless UID), such that the system may exchange data (e.g., in the form of data packets, such as Internet Protocol (IP) packets) with the wireless device. More about using electromagnetic transmitters is described herein.

The eye tracking system 22 is configured to determine a position of (one or more of the user's eyes, while the user is sitting on the seat by tracking at least one of the user's eyes. In one aspect, the eye tracking system may track (or detect) movements of the user's eyes, which may be translated into user commands for the robotic surgical system. Specifically, some detected eye movements (or gestures) may correspond to user commands. For example, upon determining that the user is staring at a particular portion of the display (e.g., for a period of time), the system may translate this gesture into a user command of zooming into that portion of the display. In this case, when the system is displaying the surgical site (captured by an endoscopic camera), the system may display a zoomed in portion of the site. In another aspect, the eye tracking system may be configured to track the user's eyes to determine whether the user is fatigued. Specifically, the system may track the user's eyes to determine the user's attention during a surgical procedure. If the user's eyes look away from the display 16 for a period of time, or the user's eyes are closed for a period of time, the system may output a notification alerting the user (e.g., by outputting a pop-up notification on the display 16 or outputting an alert audio signal through one or more speakers of the system).

In one aspect, the eye tracking system is configured to receiving sensor data from one or more sensors 23. For instance, the system 22 may receive image data captured by one or more cameras. In one aspect, the cameras may be arranged such that their field of view is directed towards the seat (or more specifically within a general vicinity of the headrest of the seat), such that images captured by the camera may include at least a portion of a user (e.g., the user's head) who is sitting on the seat. In another aspect, the system may obtain other sensor data, such as proximity sensor data from one or more proximity sensors.

To track the user's eyes, the eye tracking system is configured to determine a position of the user's eyes (e.g., while the user is sitting on the seat). In particular, the system uses the sensor data to determine the position of at least one of the user's eyes. For example, the system may perform an object recognition algorithm upon image data captured by the cameras to identify at least one eye contained therein. The system 22 may perform an eye tracking algorithm to determine eye gaze of the user. For instance, the algorithm may measure eye position and/or eye movement of at least one eye in at least one digital image captured by the camera to determine a direction (or point) of gaze with respect to a reference point. In one aspect, the eye tracking algorithm determines the direction of gaze based on optical tracking of corneal reflections. For instance, (e.g., visible, near-infrared, infrared, etc.) light is directed towards eyes of the user, causing reflections in the cornea. A camera captures the reflections, from which a direction of gaze is determined with respect to the reference point (e.g., a location on the display 16). In another aspect, the system may determine the direction of gaze based on reflections of the display 16. In some aspects, the system may determine the direction of gaze by keeping track of movements of the (e.g., pupils of the) eyes. In another aspect, the system may use any method to determine the direction of gaze of the user.

The UID tracking system 24 is configured to track (e.g., a position) of the UIDs 14. Specifically, the tracking system 25 may track the UID to ensure that the UID is within a particular range of the adjustable user console (e.g., within a threshold distance). While within the particular range, the system may enable user manipulation of the UID to control one or more robotic arms. If, however, outside the range, the system may disable the control of the robotic arm. As another example, this system may track the UID for controlling motion of a robotic arm (e.g., a robot arm actuator 17). For instance, the system may be configured to obtain sensor data from the sensors 23 that indicates the position and/or orientation of the UID, and determine spatial state signals from the sensor data. In particular, the tracking system may receive image data captured by one or more cameras, and perform object recognition to detect the UID contained within the image data. Once identified, the tracking system may generate the spatial state signals based on the UID's orientation and/or position with respect to the camera (or any other reference point). The tracking system may then transmit the spatial state signals to the controller 21, and from which the controller 21 generates control signals to control the robotic arm actuators 17, as described herein. In another aspect, the UID may transmit motion data to the tracking system indicating that the UID has moved (e.g., based on an inertial measurement unit (IMU) sensor of the UID). The tracking system may use this data to generate the spatial state signals.

In another aspect, to track the UID, the UID tracking system 24 may obtain data from the UID via one or more electromagnetic transmitters. For example, the UID tracking system may obtain input data (e.g., data indicating user input via one or more inputs (e.g., buttons) of the UID) and/or positioning data via the electromagnetic transmitters. In another aspect, the UID tracking system may track the UIDs based on the motion data (e.g., generated by IMUs integrated within the UID) and/or spatial state signals generated by (the UID tracking system or by) the UID that is contained within data packets received from the UIDs via the electromagnetic transmitters. In another aspect, the UID tracking system may track a position of a UID based on the data packets themselves. For instance, the tracking system 24 may determine the UID position based on signal strength (e.g., using Received Signal Strength Indication (RSSI)). In some aspects, the UID tracking system may perform any method to track the position of one or more UIDs.

As illustrated herein, the sensors 23 are separate devices from the eye tracking system 22 and the UID tracking system 24. In one aspect, however, one or more of the sensors may be integrated with (or a part of) one or more of the systems. For example, the electromagnetic transmitter may be a part of the UID tracking system, and one or more cameras may be a part of the eye tracking system 22. In either case, the system may be an electronic component that may be removeably coupled to the display column 15.

In one aspect, the surgical robotic system 1 may include one or more "workspaces" that are (virtual) areas (or volumes) that are each associated with an operation of a particular component of the system. Specifically, these are areas in which either 1) some components of the adjustable user console or 2) parts of the user are to be positioned during operation of the surgical robotic system in order for the adjustable user console to be in the most optimal operating configuration. For example, the system may include a 3D perception workspace in which the user may perceive an optimal 3D immersive presentation (e.g., the best stereoscopic presentation) while the user (or at least one of the user's eyes) is inside the workspace. But while outside the workspace, the user may not perceive such an optimal presentation (e.g., objects may lose depth). As another example, the system may include an eye tracking workspace in which the user's eyes (or at least one of the user's eyes) may be tracked while the user (or at least one of the user's eyes) is inside this workspace. As yet another example, the system may include a UID tracking workspace in which a UID may be tracked while held and manipulated by the user in order to control a robotic arm. Outside this workspace, the UID may be inoperable. This workspace may help prevent inadvertent movements of the robotic arm, which may occur if the user accidently drops the UID. In this case, once the user drops the UID and it travels outside the UID tracking workspace, the surgical robotic system 1 may pause (or hold) the robotic arm in place until the UID returns into the workspace.

In one aspect, the position of each of the workspaces is dependent upon a position of the workspace's associated component. For example, the position of the 3D perception workspace may be in front of the display 16, and may be dependent upon the position of the display 16. The position of the eye tracking workspace may be dependent upon the position of the eye tracking system (and/or sensors used by the system). Specifically, the eye tracking workspace may be an area that is within a field of view of at least one of the eye tracking system's cameras. The position of the UID tracking workspace may be dependent upon the position of the UID tracking system (and/or sensors used by the system). In particular, the UID tracking workspace may be an optimal area in which data packets may be exchanged between the UID and an electromagnetic transmitter of the system. In one aspect, at least some of the workspaces remain stationary with respect to the workspace's associated component. In other words, a workspace's movement may mirror movement of its associated component. For example, if the display moves (e.g., either vertically or horizontally), the 3D perception workspace may perform a similar (or proportional) movement as the display. As a result, the position of some of the workspaces may be predefined with respect to its associated component. In another aspect, the size (and shape) of each of the workspaces may be predefined, and the size of each of the workspaces may be the same or different. In another aspect, the size of at least some of the workspaces may be adjusted. For example, the size of eye tracking workspace may be dependent upon the number of cameras the eye tracking system uses to track the user's eyes—the more the cameras, the larger the workspace, since the aggregate field of view of the cameras may be larger than a single camera's point of view. More about the workspaces is described herein.

The controller 21 may be a special-purpose processor such as an application-specific integrated circuit (ASIC), a general purpose microprocessor, a field-programmable gate away (FPGA), a digital signal controller, or a set of hardware logic structures (e.g., filters, arithmetic logic units, and dedicated state machines). In one aspect, the controller may be a part of the host 18. In another aspect, the controller may be integrated into a component of the user console, such as being a part of the display column 15. In some aspects, the controller may be separate from the user console (e.g., a part of a remote server that is in communication with the user console).

The controller 21 is configured to (automatically) adjust (or configure) the adjustable user console 2 to ensure that the console has the most optimal operating configuration, while the console satisfies any ergonomic adjustments performed by the user. For example, the controller 21 is configured to determine a user-preferred position of (e.g., the user while sitting on) the seat 10. In one aspect, this may be based on a user-adjustment of the seat, or may be based on a determined location of a body part of the user (e.g., the user's eyes), while the user sits on the seat. Once the user has defined the user-preferred position, the controller is configured to determine whether the adjustable user console is in an optimal operating configuration. Specifically, the controller may determine whether each (or at least some) of the workspace requirements are satisfied (e.g., the user's eyes being inside the 3D perception workspace). If not, the controller is configured to adjust (or reconfigure) the adjustable user console. For instance, in the case of the 3D perception workspace, when the user's eyes are not inside the workspace, meaning that the display may not be properly aligned with the user's eyes, the controller may transmit control signals to the display column in order to adjust the display (e.g., in $DoF_1$ and/or $DoF_2$). More about the operations performed by the controller is described herein.

In one aspect, the controller 21 may be configured to monitor (or keep track) of a current configuration of the adjustable user console 2. In particular, the controller may determine the position and/or orientation of each of the components of the adjustable user console, and may store the information in local memory.

Figure 4:
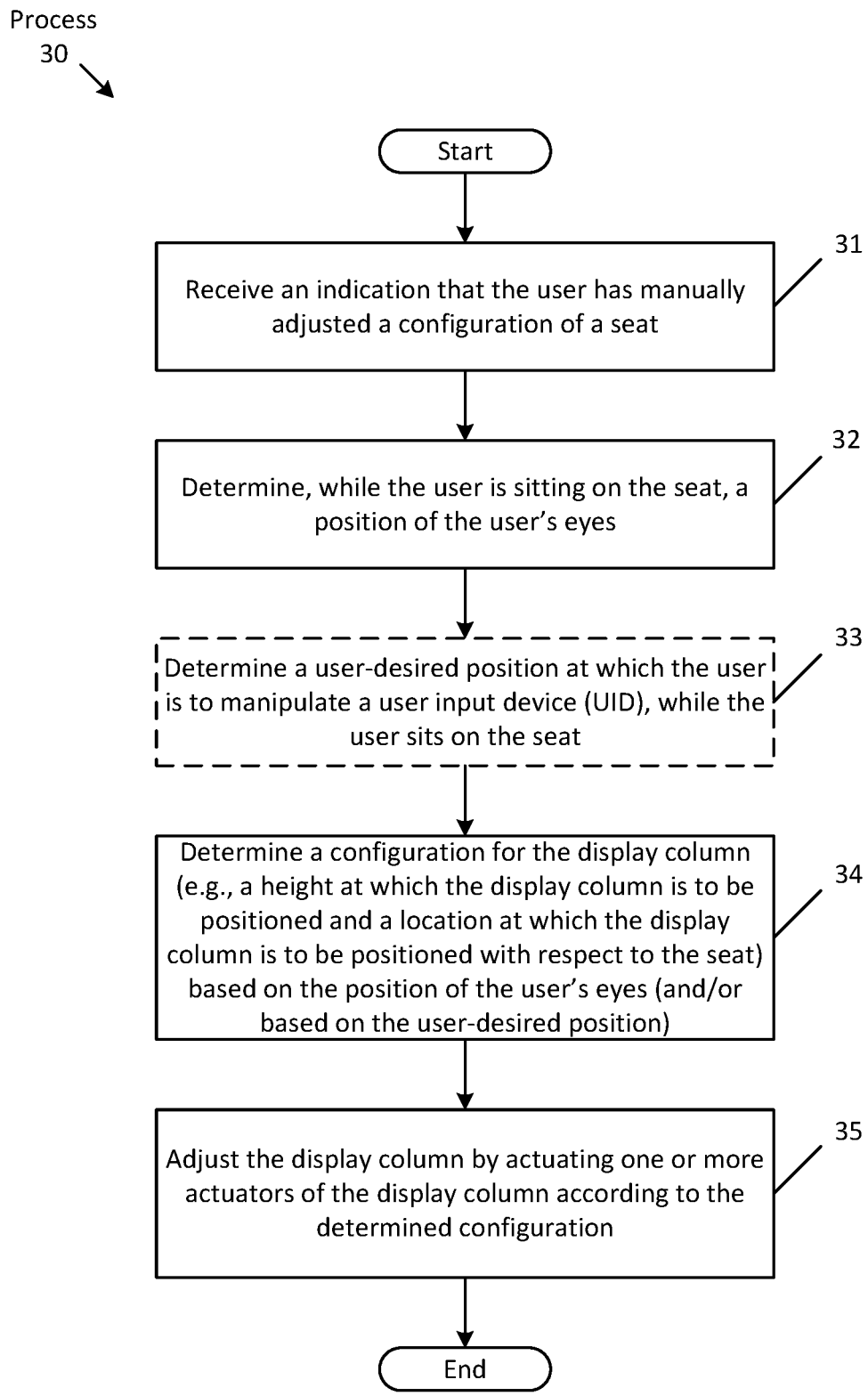
FIG. 4 is a flowchart of a process for configuring the adjustable user console based on the user manually adjusting the seat.

FIG. 4 is a flowchart of a process 30 for configuring the adjustable user console based on the user manually adjusting the seat. In one aspect, the process may be performed during an initial setup of the surgical robotic system 1. For example, the process may be performed before the user begins performing a surgical procedure, but while the user is in a position at which the user will be performing the surgical procedure, such as sitting on the seat, with the user's arms on the armrests of the seat. In another aspect, at least some of the operations may be performed while the system is in use. In some aspects, the process 30 may be performed by the (adjustable user console 2 of the) surgical robotic system 1. Specifically, at least a portion of the process may be performed by the controller 21. In another aspect, at least a portion of the process may be performed by the eye tracking system 22 and/or the UID tracking system 24. Accordingly, this figure will be described with reference to FIGS. 1-3.

The process 30 begins by receiving an indication that the user has manually adjusted the seat 10 (at block 31). In one aspect, the indication may be received in response to the adjustable user console 2 receiving a user command (as user input) to adjust at least one degree of freedom of the seat. Specifically, when the user manipulates a control console to adjust the height of the seat (e.g., $DoF_8$, as shown in FIG. 2), the controller 21 may obtain a control signal from the control console as the indication. In another aspect, the indication may indicate that the user has finished adjusting the seat to a user-preferred position. For instance, upon completing the adjustment of the configuration of the seat, the controller 21 may receive a user command (e.g., a user-selection of a UI item of a GUI displayed on the display 16, a manipulation of a UID, a voice command, etc.) that indicates that the initial setup of the seat (or user console) is complete.

In another aspect, the indication may indicate that the user has manually adjusted the configuration of other components of the adjustable user console 2. For example, the indication may be received when the user has manually adjusted the display column 15, the foot pedal 13, the seat 10, and/or a combination therein.

The process 30 determines, using the eye tracking system and while the user is sitting on the seat 10, a position of the user's eyes (at block 32). In one aspect, this operation may be performed in response to receiving the indication. As described herein, the eye tracking system 22 may receive image data captured by one or more cameras, and use the data to identify the position of the user's eyes within the field of view of the camera. In one aspect, the position of the user's eyes may be determined through other methods in lieu of or in addition to using eye tracking. For example, the position of the user's eyes may be determined based on one or more anthropometric measurements of the user. Specifically, the system may determine (or estimate) the position of the user's eyes based on quantitative measurements of at least a portion of the user's body. For example, the system may be configured to determine anthropometric measurements of the user (e.g., a height of the user, a height of the user's torso, a length of the user's arms, etc.) using image data captured by one or more cameras of the user console 2. In one aspect, the anthropometric measurements may be determined via user input (e.g., based on user settings that indicate a user's measurements). In one aspect, the system may include an anthropometric model (or algorithm) that is derived in a controlled environment (e.g., a laboratory) that estimates the position and/or measurements of a user who is sitting on the seat based on measurements of a test group. In one aspect, the model may be derived by a machine learning algorithm. In this case, the eye tracking system may input one or more anthropometric measurements (or image data) into the model, which in response may output the estimated position of the user's eyes.

In one aspect, anthropometric measurements may be indirectly determined by the eye tracking system. Specifically, the measurements may be estimated based on the configuration of the seat (and/or the foot pedals). For example, the system may determine the configuration of the seat based on control signals produced by the controller 21 and/or other components of the user console 2, while (or after) the user manually adjusts the seat. From the (adjusted) configuration, the system may determine the anthropometric measurements, for example a height of a user may be based on a base height, which is the height of the base 56 from the platform 58, and/or an armrest height, which is the height of the armrest 54 from the base 56, as shown in FIG. 2. In another aspect, the system may use the configuration of the seat as input into the model to determine the position of the user's eyes. In another aspect, the model described herein may output other positions and/or orientations of other parts of the user's body, such as the user's entire head and hands.

The process 30 determines a user-desired position for a UID at which the user is to (hold and) manipulate the UID, while the user sits on the seat 10 (at block 33). As described herein, the UID is arranged to control a robotic arm when held and manipulated by the user. In one aspect, a user-desired position may be a location (or area) at which the user is to hold and manipulate the UID while performing the surgical procedure. For instance, the user-desired position may extend beyond (e.g., by a threshold distance) the armrest 54 and extending away from the backrest 55. This position may be an ergonomic position that may be the most comfortable position at which the user will use the UID. In one aspect, this position may be determined, according to the adjusted configuration of the seat. Specifically, the controller 21 may receive the configuration of the seat, such as the base height and the armrest height, and may determine (or estimate) the user-desired position for the UID based on these heights. For instance, the controller 21 may perform a table lookup using the base height and armrest height into a data structure that associates pre-defined user-desired positions with base heights and armrest heights, and select the user-desired position that is associated with the current configuration of the seat. In one aspect, to make this determination the system may use the user console configuration model, as described herein.

In another aspect, the UID tracking system may determine the user-desired position. For example, while sitting on the seat, the user may position the UID at the position at which the user is to manipulate the UID during the surgical procedure (e.g., at a position between the armrest 54 of the seat 10 and the display column 15). The UID tracking system may determine the position of the UID, as described herein. The controller 21 may receive an indication of a user-selection defining the position of the UID as the user-desired position. For example, once the user has positioned the UID at the position, the controller may receive a user command (e.g., via a user-selection of a control of the UID or a voice command), that this position is the preferred position.

The process 30 determines a configuration (e.g., a height at which the display column 15 is to be positioned (e.g., along $DoF_1$) and a location at which the display column is to be positioned with respect to the seat 10) based on the position of the user's eyes (at block 34). In one aspect, the display column may be configured (or orientated) such that the position of the user's eyes is inside the 3D perception workspace and/or the eye tracking workspace. Specifically, the controller 21 may be configured to determine how (or whether) to configure the display column such that the position of the user's eyes is (or remains) inside the workspaces. In one aspect, the controller may be configured to determine the position of the 3D perception workspace and/or the position of the eye tracking workspace. To do this, the controller determines a current configuration of the display column (e.g., a current height and a current location with respect to the seat 10). In one aspect, the controller may determine the positions of the workspaces from the current configuration, since the components associated with the workspaces may be coupled to (or mounted on) the display column. For instance, the display 15 of which the 3D perception workspace is associated is mounted on top of the vertical support and is directed towards the seat 10. In addition, the eye tracking system (and/or the system's cameras) of which the eye tracking workspace is associated, may also be mounted to the display column (e.g., coupled to the display or the vertical support). With the current configuration, the controller determines the position of the at least one of the workspaces (e.g., a first workspace). The controller (or the eye tracking system) determines whether the eyes of the user are outside of either the 3D perception workspace or the eye tracking workspace (e.g., based on a comparison of the position of the user's eyes and the position of the workspaces). If so, the controller determines a new configuration (e.g., a new height and a new distance) by determining an adjustment to the display column such that the position of the user's eyes is inside at least one of the workspaces.

In one aspect, the controller 21 may be configured to further determine the configuration based on the user-desired position of the UID. Specifically, the controller may be configured to determine how (or whether) to configure the display column such that the user-desired position is (or remains) inside the UID tracking workspace. In one aspect, this determination may be made in combination with (or separate from) determining how to configure the display column such that the position of the user's eyes in in the 3D perception workspace and/or the eye tracking workspace, as previously mentioned. In this case, the UID tracking system 24 may be coupled to the (vertical support 50 of the) display column 15. Thus, with the current configuration, the controller determines the position of the UID tracking workspace (e.g., the second workspace). The controller (or the UID tracking system) determines whether the user-desired position (and/or the UID) is outside of the UID tracking workspace If so, the controller determines a new configuration of the display column such that the UID (and/or the user-preferred position) is inside the UID tracking workspace. As described herein, this operation may be performed in addition to the operations described above to determine the new configuration. Thus, the new configuration may be determined such that at least one adjustment is performed by the display column such that the position of the user's eyes is inside the 3D perception workspace and/or the eye tracking workspace and the user-desired position of the UID is inside the UID tracking workspace.

The process 30 adjusts the display column 15 by actuating one or more actuators 25 of the display column according to the determined configuration (at block 35). In one aspect, the configuration may define characteristics of the adjustable user console, such as a height of the display 16 and/or a location of the display column 15 with respect to the seat. In particular, the controller 21 is configured to signal (or transmit a control signal) at least one actuator of the display column to adjust the display column. For example, the one or more adjustments described herein may include 1) a vertical movement of the display along a vertical axis that runs through the display column and/or 2) a displacement of the display column with respect to the seat. Specifically, the controller may signal 1) at least one (first) actuator 25 to move the display along the vertical axis (Y-axis) to a height defined by the configuration and/or 2) at least one (second) actuator to move the display column along the horizontal axis (X-axis) such that the display column is moved to a new location (e.g., further apart from the seat). Thus, by adjusting the configuration of the display column, the controller adjusts the position of workspaces that are associated with components that are mounted (or a part of) the column. As described herein, movement of workspaces may mirror their associated components. As a result, the adjustment of the display column may move at least one of the 3D perception workspace, the eye tracking workspace, and the UID tracking workspace.

Some aspects perform variations of the process 30. For example, the specific operations of the process may not be performed in the exact order shown and described. The specific operations may not be performed in one continuous series of operations and different specific operations may be performed in different aspects. For example, the controller 21 may determine how to configure the display column, based on other features of the user, such as other facial features (e.g., nose, mouth, etc.) or body features (e.g., the user's head, etc.). In another aspect, the controller 21 may configure other components of the adjustable user console 2. In this case, the controller may perform at least some of the operations of process 30 for these components. For instance, in response to user manipulation of the user console (e.g., adjusting the configuration of the seat 10), the controller may determine how (or whether) to configure the foot pedal 13. In this example, the controller may configure the pedal based on any method described herein (e.g., the position of the user's eyes, the configuration of the seat, or anthropometric measurements of the user). Thus, the controller may adjust at least one of the degrees of freedom of the foot pedal (e.g., tilting the foot pedal along $DoF_4$ and/or moving the foot pedal with respect to the seat along $DoF_3$) according to the anthropometric measurements of the user, for example. In this case, the controller may move the foot pedal away from the seat, if it is determined that the user is taller than another user who had previously used the user console. To adjust the foot pedal, the controller is configured to 1) signal at least one (first) actuator of the foot pedal to tilt the pedal and/or 2) signal at least one (second) actuator of the foot pedal to move the pedal closer or further away from the seat.

Figure 5:
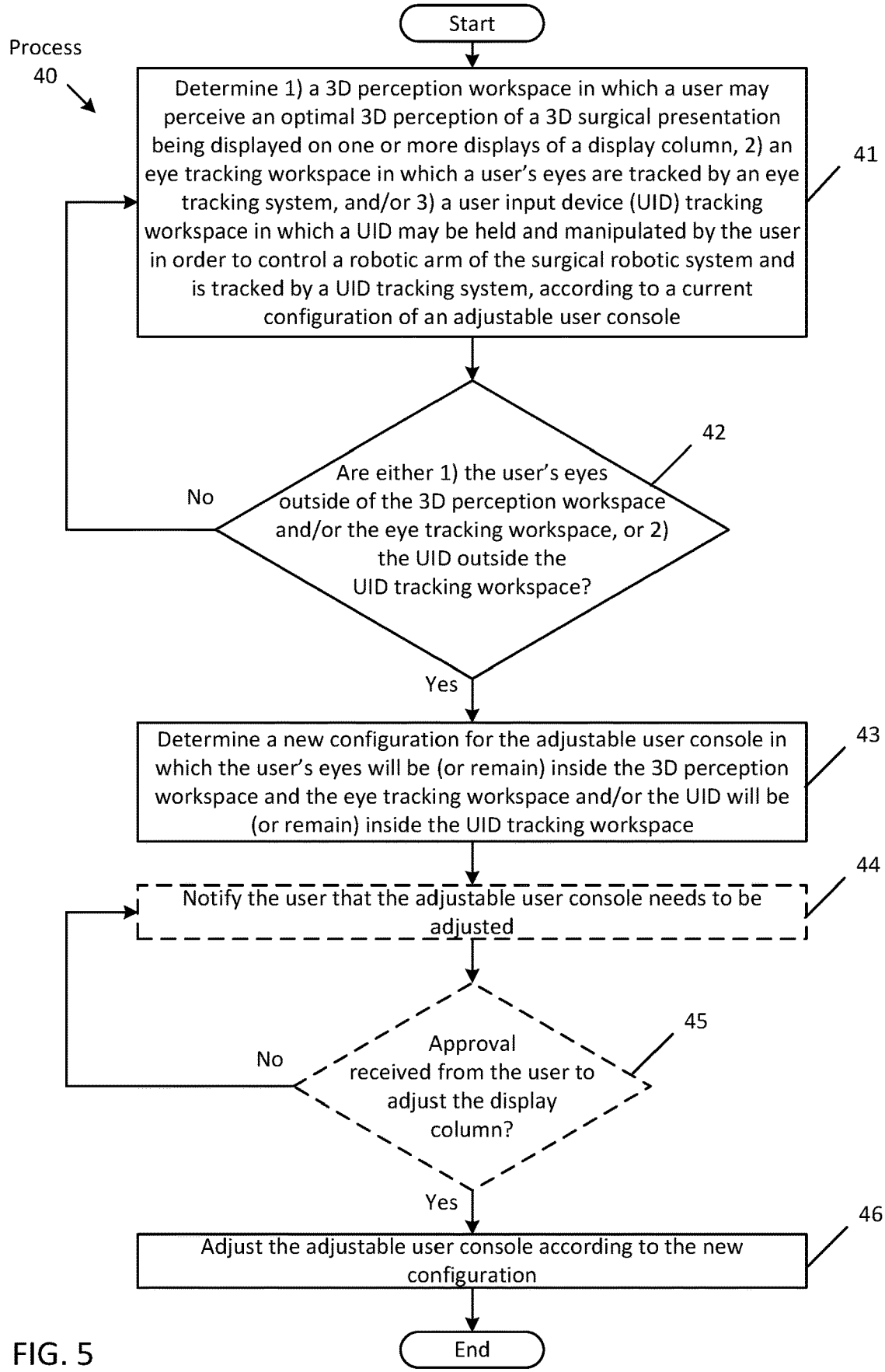
FIG. 5 is a flowchart of a process for automatically configuring the adjustable user console based upon a determination in which the user of the adjustable user console is not aligned with one or more workspaces.

FIG. 5 is a flowchart of a process 40 for automatically configuring the adjustable user console based upon a determination in which the user of the adjustable user console is not aligned with one or more workspaces. For instance, this process may be performed (e.g., in real-time) while the user is performing a surgical procedure. In another aspect, at least some of the operations may be performed during the initial setup of the user console. This process may be performed by the (adjustable user console 2 of the) surgical robotic system 1. Specifically, at least a portion of the process may be performed by the controller 21, the eye tracking system 22, and/or the UID tracking system 24. Accordingly, this figure will be described with reference to FIGS. 1-3.

The process 40 determines 1) a 3D perception workspace in which a user may perceive an optimal 3D perception of a 3D surgical presentation being displayed on one or more displays 16 of a display column 15, 2) an eye tracking workspace in which a user's eyes are tracked by the eye tracking system 22, and/or 3) a UID tracking workspace in which a UID may be held and manipulated by the user in order to control a robotic arm of the surgical robotic system 1, and is tracked by the UID tracking system 24, according to a current configuration of an adjustable user console (at block 41). As described herein, the controller 21 determines the current configuration, of one or more components of the user console, such as the seat 10, the display column 15, and the foot pedal 13. For instance, with respect to the display column, the controller may determine a current height of the display 16 of the display column and/or a location of the display column with respect to the seat (e.g., a distance between the display column and the seat). From the current configuration and the position of the 1) one or more displays, 2) the eye tracking system, and 3) the UID tracking system, the controller determines each of the workspaces. In particular, the controller determines characteristics of the workspaces, such as positions, orientations, and/or sizes of the workspaces. In one aspect, at least some of the characteristics may be with respect to the seat 10 of the user console 2. In another aspect, characteristics of workspaces may be predefined (or defined) based on a location (position) of its associated component, as described herein.

The process determines whether 1) the user's eyes are outside the 3D perception workspace and/or the eye tracking workspace, and/or 2) the UID is outside the UID tracking workspace (at decision block 42). For instance, the eye tracking system 22 may determine the position of the user's eyes (e.g., based on object recognition, as described herein) and the UID tracking system 24 may determine the position of the UID, and the controller 21 determines whether the position of the user's eyes and/or the position of the UID is outside any of their respective workspaces. In one aspect, the user's eyes may be outside of their respective workspaces and/or the UID may be outside the UID tracking workspace for many reasons. For instance, the user may have repositioned the user's body or may have adjusted the user's seat and/or foot pedal. If so, the process 40 determines a new configuration for the adjustable user console in which the user's eyes will be (or remain) inside the 3D perception workspace and the eye tracking workspace, and/or the UID will be (or remain) inside the UID tracking workspace (at block 43). Specifically, the controller may determine how to configure the display column 15, such as determining a new height of the display 16 and/or a new location for the display column with respect to the seat, such that the user console is in an optimal operating configuration (e.g., the eyes of the user are inside the 3D perception workspace and the eye tracking workspace, and the UID is inside the UID tracking workspace), as described herein.

The process 40 notifies the user that the adjustable user console (e.g., the display column) needs to be adjusted according to the new configuration (at block 44). Specifically, the controller 21 notifies the user that an adjustment is required in order to maintain an optimal operating configuration. This ensures that the user will be aware of a potential adjustment, in order for the user to prepare for the adjustment. For instance, the controller 21 may output a visual notification, such as outputting a pop-up notification on the display 16. The controller may output an audible notification, such as outputting an alert audio signal through one or more speakers.

The process 40 determines whether an approval has been received from the user to adjust the adjustable user console (at decision block 45). In one aspect, approval may be based on a user selection of a UI item displayed within a GUI of the display. In another aspect, the approval may be based on a user-manipulation of the UID (e.g., selection of a control). If approved (e.g., in response to receiving an indication of an approval), the process 40 adjusts the adjustable user console according to the new configuration by actuating one or more actuators of the adjustable user console. (at block 46). As described herein, the controller may adjust the console by signaling one or more actuators of the display column to at least one of 1) vertically move the display of the display column along a vertical axis to a new height and 2) displace the (e.g., entire) display column with respect to the seat (e.g., by moving the display column along a horizontal axis to separate the column from the seat by a new distance), according to the new configuration. In one aspect, adjusting the display column moves at least one of the workspaces to a new position (e.g., with respect to the seat 10).

Some aspects perform variations of the process 40. For example, the specific operations of the process may not be performed in the exact order shown and described. The specific operations may not be performed in one continuous series of operations and different specific operations may be performed in different aspects.

In one aspect, at least some of the operations of processes 30 and 40 may be optional (illustrated as dashed boxes), and therefore may be omitted from a process. For instance, the process 30 may omit the operations of 33. In this case, the process 30 may adjust the display column according to a determined height and distance based on the position of the user's eyes, and without taking into consideration the user-desired position of the UID. As another example, the process 40 may omit either of the operations 44 and 45. As a result, when omitted, the process may adjust the adjustable user console, without requiring approval from the user. Thus, the adjustable user console may be configured (and reconfigured) automatically (e.g., without user intervention), while the user is using the console (e.g., during at least a portion of a surgical procedure).

In one aspect, at least some of the operations described herein in processes 30 and 40 may be performed while the user's eyes and/or the UIDs remain within their respective workspaces. In this case, rather than determining a new configuration in response to determining that the user's eyes are outside the 3D perception workspace and/or the eye tracking workspace, the controller may perform this determination once the user's eyes are within a threshold of a boundary of either workspace. For example, the controller 21 may determine whether the position of the user's eyes is within a threshold distance (e.g., six inches) from a (e.g., virtual) boundary of the 3D perception workspace (and/or the eye tracking workspace), and may determine whether the user-desired position (of the UID) is within the (e.g., same or different) threshold distance from a boundary of the UID tracking workspace. The controller 21 may be configured to determine a new configuration in response to determining that at least one of 1) the user's eyes are within a (e.g., first) threshold distance (e.g., six inches) from a (e.g., virtual) boundary of the 3D perception workspace (and/or the eye tracking workspace and 2) the UID is within another (e.g., second) threshold distance (which may be the same or different than the first threshold distance) from the boundary of the UID tracking workspace. In one aspect, the eye tracking workspace may have a different threshold distance requirement than the 3D perception workspace. As a result of being within that threshold distance, the controller 21 may be configured to determine an adjustment such that the user's eyes remain inside the workspace and beyond the threshold distance. This may ensure that the user's eyes remain within an optimal region of the workspace, without leaving the workspace entirely to determine an adjustment. In some aspects, the controller may perform these operations based on whether the user's eyes are within the threshold distance for a threshold period of time (e.g., one minute). In another aspect, each of the workspaces may have similar (or different) threshold distances and/or similar (or different) threshold periods of time.

As described herein, the controller 21 is configured to adjust the adjustable user console, specifically the display column 15 according to the determined (new) configuration in order for the user's eyes and/or UID(s) to remain in their respective workspaces. In one aspect, however, the controller may be configured to adjust several separate electronic devices according to the configuration. As described herein, at least some of the systems (e.g., the UID tracking system 24 and/or the eye tracking system 22) may be a part of separate electronic devices. In this case, upon determining the new configuration, the controller 21 may be configured to signal one or more actuators of those separate electronic devices to perform at least one adjustment. For example, when the UID tracking system is a part of a separate electronic device and the UID is determined to be outside the UID tracking workspace, the controller 21 may signal the device to perform one or more adjustment (e.g., moving to a new location), such that the UID tracking workspace moves to a new location in which the UID is inside the workspace.

Figure 6C:
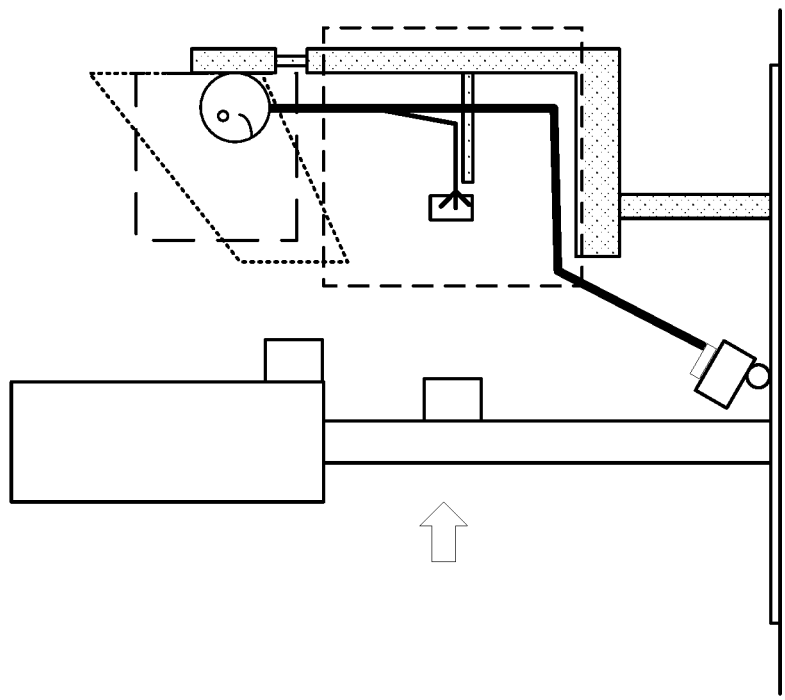
Figure 6B:
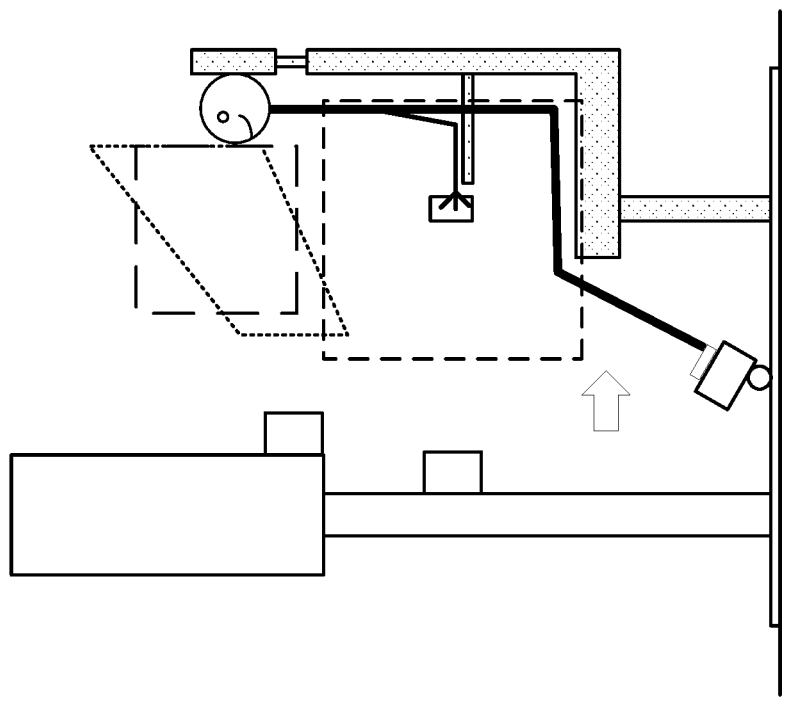

FIGS. 6A-6C show several stages in which the adjustable user console 2 is automatically configured according to one aspect. Specifically, these figures illustrate a progression of operations in which a user performs ergonomic adjustments to the user console, and, in response the user console is automatically configured such that the console is in an optimal operating configuration.

FIG. 6A illustrates the user sitting on the seat 10, holding the UID 14, while the user's feet are positioned on the foot pedal 13. In one aspect, this stage represents the initial setup of the adjustable user console in which the user has just sat down onto the seat to perform ergonomic adjustments, as described herein. As shown, however, the user console is not appropriately configured for this user. For example, the foot pedal 13 is too close to the seat, such that the user's knees are bending upward. This may be due to the fact that the adjustable user console was previously configured by a user who is shorter than the current user. As a result, the current user may find this configuration to be uncomfortable.

This figure also shows the display column 15 that includes the display 16, the eye tracking system 22, and the UID tracking system 24, and their respective workspaces. As illustrated, the eye tracking system is coupled to the display (or the bottom of the display), and the UID tracking system is coupled on the vertical support 50 of the column. In one aspect, these systems may be stationary (e.g., fixedly coupled) to the display column. In another aspect, either of these systems may be movably (or removeably) coupled to the display column, such that their positions may be adjusted.

Each of the workspaces are illustrated as quadrilateral shapes (or boundaries) that include portions of the seat 10 and the user. In one aspect, each of the workspaces may any shape (e.g., rectangular, circular, etc.). In another aspect, each of the workspaces may be three-dimensional shapes (e.g., cuboid, cylinder, etc.). As shown, the position of the user's eyes is inside the 3D perception workspace 51 and the eye tracking workspace 52, both of which at least partially overlap. In addition, the UID that is being held by the user is inside the UID tracking workspace 53.

FIG. 6B illustrates that the user has performed an ergonomic adjustment. Specifically, the user has moved the seat base 56 away from the display column 15 and the foot pedal 13 (along $DoF_5$). The user has made this adjustment in order to comfortably sit on the seat, while the user's feet are positioned on the foot pedal (shown by the user's knees no longer being bent in the air). As a result of the adjustment, however, the position of the user's eyes and the UID have shifted away from the display column. Thus, the position of the user's eyes is outside the 3D perception workspace 51 and the eye tracking workspace 52. Specifically, at this position, the user may not view the most optimal 3D presentation and the eye tracking system 22 may be unable to effectively track the user's eyes.

FIG. 6C illustrates an automatic adjustment to the configuration of the adjustable user console 2. Specifically, upon determining that the user's eyes are outside the 3D perception workspace and the eye tracking workspace, the controller 21 may determine a new configuration of the user console. In this case, the controller determines that the distance between the display column and the seat should be reduced in order to compensate for the ergonomic adjustment by the user. As a result, the controller signals one or more actuators of the display column 15 to move the display column (along $DoF_2$) towards the user in order for the user's eyes to remain inside both workspaces.

As previously explained, an aspect of the disclosure may be a non-transitory machine-readable medium (such as microelectronic memory) having stored thereon instructions, which program one or more data processing components (generically referred to here as a "processor") to automatically adjust (or configure) the adjustable user console 2 to ensure that the console has the most optimal operating configuration, while the console satisfies any ergonomic adjustments performed by the user. In other aspects, some of these operations might be performed by specific hardware components that contain hardwired logic. Those operations might alternatively be performed by any combination of programmed data processing components and fixed hardwired circuit components.

While certain aspects have been described and shown in the accompanying drawings, it is to be understood that such aspects are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some aspects, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some aspects, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. An adjustable user console for a surgical robotic system comprising:
    a display for displaying a three-dimensional (3D) surgical presentation;
    an eye tracking system for tracking eyes of a user;
    one or more actuators coupled to the display;
    at least one processor; and
    memory having stored therein instructions which when executed by the at least one processor causes the adjustable user console to:
        determine 1) a 3D perception workspace for the display and 2) an eye tracking workspace for the eye tracking system according to a current configuration of the adjustable user console, wherein the 3D perception workspace and the eye tracking workspace are both different volumes of space in front of the display,
        determine, using the eye tracking system, whether the eyes of the user are outside either of the 3D perception workspace or the eye tracking workspace,
        in response to determining that the eyes of the user are outside either the 3D perception workspace or the eye tracking workspace, determine a new configuration for the adjustable user console in which the eyes of the user are inside the 3D perception workspace and the eye tracking workspace, and
        adjust the display according to the new configuration by actuating the one or more actuators.

2. The adjustable user console of claim 1 further comprising:
    a handheld user-input device (UID) for controlling the surgical robotic system; and
    a UID tracking system for tracking the handheld UID,
    wherein the memory has stored therein further instructions to determine a UID tracking workspace for the handheld UID,
    wherein the new configuration is determined such that the handheld UID is or remains inside the UID tracking workspace in response to the adjusted display.

3. The adjustable user console of claim 2, wherein the memory has stored therein further instructions to determine, using the UID tracking system, whether the handheld UID is outside the UID tracking workspace,
    wherein the new configuration is determined in response to determining that at least one of 1) the eyes of the user are outside either the 3D perception workspace or the eye tracking workspace and 2) the handheld UID is outside the UID tracking workspace such that the eyes of the user remain inside the 3D perception workspace and the eye tracking workspace and the handheld UID remains inside the UID tracking workspace.

4. The adjustable user console of claim 3, wherein determining whether the eyes of the user are outside either the 3D perception workspace or the eye tracking workspace and determining whether the handheld UID is outside the UID tracking workspace comprises determining whether the eyes of the user are within a first threshold distance from a boundary of the 3D perception workspace and a boundary of the eye tracking workspace and determining whether the handheld UID is within a second threshold distance from a boundary of the UID tracking workspace for a threshold period of time.

5. The adjustable user console of claim 1, wherein the instructions to adjust the display comprises instructions to move the display along at least one of a plurality of axes.

6. The adjustable user console of claim 5 further comprises a display column to which the display is coupled, wherein the instructions to move the display comprises instructions to at least one of 1) vertically move the display along the display column and 2) displace the display column.

7. The adjustable user console of claim 1, wherein the memory has further instructions to notify the user that the adjustable user console needs to be adjusted, wherein the adjustable user console is adjusted according to the new configuration in response to receiving an indication of an approval to adjust the adjustable user console from the user.

8. An apparatus comprising:
    a display column that has:
        a display for displaying a three-dimensional (3D) surgical presentation,
        an eye tracking system for tracking eyes of a user, and
        one or more actuators; and
    a controller that is configured to 1) determine a 3D perception workspace for the display and an eye tracking workspace for the eye tracking system according to a current configuration of the apparatus, 2) determine, using the eye tracking system, whether the eyes of the user are outside either of the 3D perception workspace or the eye tracking workspace, 3) responsive to determining that the eyes of the user are outside either the 3D perception workspace or the eye tracking workspace, determine a new configuration for the apparatus in which the eyes of the user are inside the 3D perception workspace and the eye tracking workspace, 4) and adjust the display according to the new configuration by actuating the one or more actuators, wherein the 3D perception workspace and the eye tracking workspace are both different volumes of space in front of the display.

9. The apparatus of claim 8 further comprising:
    a handheld user-input device (UID) for controlling a robotic arm; and
    a UID tracking system for tracking the handheld UID,
    wherein the controller is configured to determine a UID tracking workspace for the handheld UID,
    wherein the new configuration is determined such that the handheld UID is or remains inside the UID tracking workspace in response to the adjustment to the display.

10. The apparatus of claim 9, wherein the controller is configured to determine, using the UID tracking system, whether the handheld UID is outside the UID tracking workspace,
    wherein the new configuration is determined in response to determining that at least one of 1) the eyes of the user are outside either the 3D perception workspace or the eye tracking workspace and 2) the handheld UID is outside the UID tracking workspace such that the eyes of the user remain inside the 3D perception workspace and the eye tracking workspace and the handheld UID remains inside the UID tracking workspace.

11. The apparatus of claim 10, wherein determining whether the eyes of the user are outside either the 3D perception workspace or the eye tracking workspace and determining whether the handheld UID is outside the UID tracking workspace comprises determining whether the eyes of the user are within a first threshold distance from a boundary of the 3D perception workspace and a boundary of the eye tracking workspace and determining whether the handheld UID is within a second threshold distance from a boundary of the UID tracking workspace for a threshold period of time.

12. The apparatus of claim 8, wherein adjusting the display comprises moving the display column along at least one of a plurality of axes.

13. The apparatus of claim 12 further comprises a seat, wherein moving the display comprises at least one of 1) vertically move the display along the display column and 2) displace the display column with respect to the seat.

14. The apparatus of claim 8, wherein the controller is configured to notify the user that the apparatus needs to be adjusted, wherein the controller is configured to adjust the display according to the new configuration in response to receiving an indication of an approval to adjust the apparatus from the user.

15. A method for adjusting an adjustable user console of a surgical robotic system, the method comprises:
    determining 1) a three-dimensional (3D) perception workspace for a display of the adjustable user console and 2) an eye tracking workspace for an eye tracking system of the adjustable user console, according to a current configuration of the adjustable user console, wherein the 3D perception workspace and the eye tracking workspace are both different volumes of space in front of the display;
    determining, using the eye tracking system, whether eyes of a user are outside either the 3D perception workspace or the eye tracking workspace;
    in response to determining that the eyes of the user are outside either the 3D perception workspace or the eye tracking workspace, determining a new configuration for the adjustable user console in which the eyes of the user are inside the 3D perception workspace and the eye tracking workspace; and
    adjusting the adjustable user console according to the new configuration by actuating one or more actuators of the display or a seat of the adjustable user console.

16. The method of claim 15,
    wherein the adjustable user console comprises a handheld user-input device (UID) for controlling the surgical robotic system and a UID tracking system for tracking the handheld UID,
    wherein the method further comprises determining a UID tracking workspace for the handheld UID,
    wherein the new configuration is determined such that the handheld UID is or remains inside the UID tracking workspace in response to the adjustment to the adjustable user console.

17. The method of claim 16 further comprises determining, using the UID tracking system, whether the handheld UID is outside the UID tracking workspace,
    wherein the new configuration is determined in response to determining that at least one of 1) the eyes of the user are outside either the 3D perception workspace or the eye tracking workspace and 2) the handheld UID is outside the UID tracking workspace such that the eyes of the user remain inside the 3D perception workspace and the eye tracking workspace and the handheld UID remains inside the UID tracking workspace.

18. The method of claim 17, wherein determining whether the eyes of the user are outside either the 3D perception workspace or the eye tracking workspace and determining whether the handheld UID is outside the UID tracking workspace comprises determining whether the eyes of the user are within a first threshold distance from a boundary of the 3D perception workspace and a boundary of the eye tracking workspace and determining whether the handheld UID is within a second threshold distance from a boundary of the UID tracking workspace for a threshold period of time.

19. The method of claim 15, wherein adjusting the adjustable user console comprises moving the display along at least one of a plurality of axes.

20. The method of claim 19, wherein the adjustable user console comprises a display column to which the display is coupled, wherein moving the display comprises at least one of 1) vertically moving the display along the display column and 2) displacing the display column.

21. The method of claim 15 further comprising notifying the user that the adjustable user console needs to be adjusted, wherein the adjustable user console is adjusted according to the new configuration in response to receiving an indication of an approval to adjust the adjustable user console from the user.

* * * * *